(12) United States Patent
Barclay

(10) Patent No.: US 6,322,750 B1
(45) Date of Patent: Nov. 27, 2001

(54) GAS DETECTOR INDICATOR STRIP PROVIDING ENHANCED DYNAMIC RANGE

(75) Inventor: L. Harvey Barclay, Houston, TX (US)

(73) Assignee: Robert L. Kimbell, Houston, TX (US)

( * ) Notice: Subject to any disclaimer, the term of this patent is extended or adjusted under 35 U.S.C. 154(b) by 0 days.

(21) Appl. No.: 09/223,213

(22) Filed: Dec. 30, 1998

(51) Int. Cl.<sup>7</sup> ................................................. G01N 33/48
(52) U.S. Cl. ............................. 422/56; 422/61; 436/164; 436/169; 436/121
(58) Field of Search ............... 422/56, 61; 436/119–121, 436/164, 169

(56) References Cited

U.S. PATENT DOCUMENTS

| | | | |
|---|---|---|---|
| 2,232,622 | * | 2/1941 | Moses et al. ........................... 422/56 |
| 3,507,269 | * | 4/1970 | Berry ................................... 436/121 |
| 4,032,297 | * | 6/1977 | Lyshkow ............................. 436/121 |
| 4,174,202 | * | 11/1979 | Simpson ................................. 422/56 |
| 4,398,183 | * | 8/1983 | Ando ................................... 340/500 |
| 5,310,525 | * | 5/1994 | Churchouse et al. .................. 422/56 |

* cited by examiner

Primary Examiner—Lyle A. Alexander
(74) Attorney, Agent, or Firm—Bracewell & Patterson, L.L.P.

(57) ABSTRACT

The present disclosure is a tape responsive to gases. One version is paper impregnated with lead acetate, a backing layer of impervious sheet material, and a top face pervious, transparent layer. The top layer retards gas exposure and expands the range of sensitivity. The top layer is preferably pervious, transparent and has a thickness and width to control exposure.

14 Claims, 1 Drawing Sheet

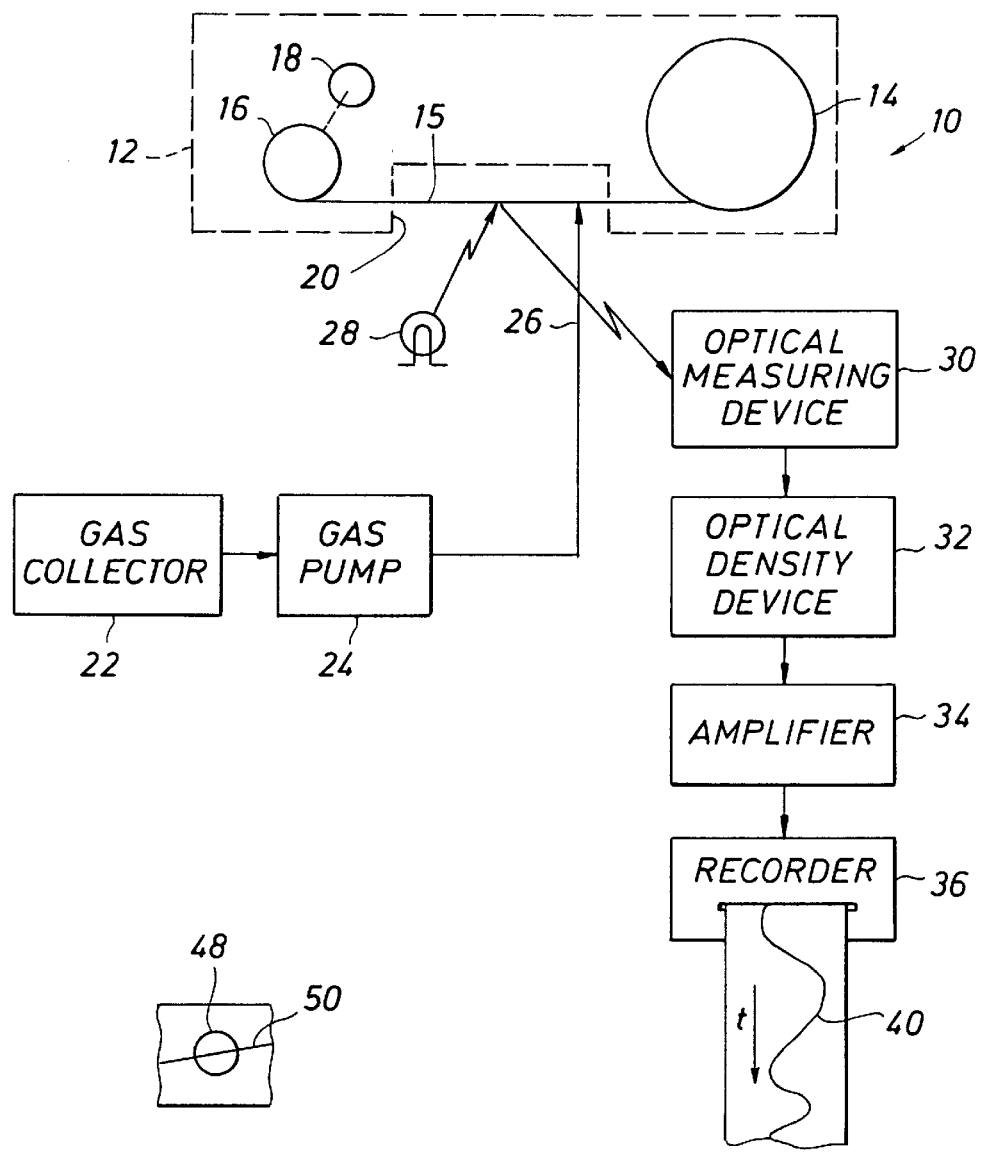
FIG. 1
FIG. 3
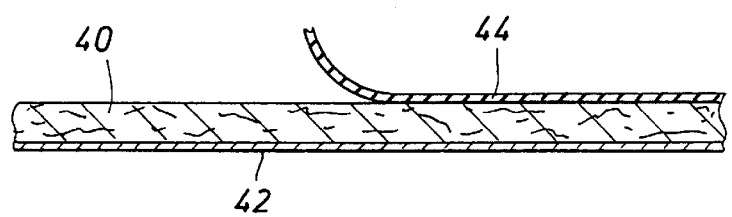
FIG. 2

GAS DETECTOR INDICATOR STRIP PROVIDING ENHANCED DYNAMIC RANGE

BACKGROUND OF THE DISCLOSURE

There are many detectors for gases which use indicator or detector strips. These strips are exposed to the atmosphere where a suspected gas might be located. If a suspected gas is in the air, then the exposed strip will provide a change in color which is converted into gas concentration. The example that will be used below is a strip of tape which is responsive to hydrogen sulfide ($H_2S$). The hydrogen sulfide gas indicator strip is normally made of lead acetate which is impregnated into the fibers of the paper strip. The strip is normally formed of a porous fiber base, paper being the preferred form, typically using a strip of one quarter to one half inch in width. The strip typically is paper, and is comprised of a layer of cellulose fibers which are matted into the paper of specified thickness and width. After fabrication of the paper strip, it is impregnated with a solvent which carries the lead acetate. The solvent can be water or the like.

On exposure to $H_2S$, the lead acetate strip changes color. This color change is indicated by an optical densitometer. At one end of the scale, the white level provides a first data point and at the other end of the scale, the black intensity provides the other end point. Between the two end points, the scale of the optical density is defined. This yields a range which has to be correlated with other factors. The range at the black end indicates maximum exposure to $H_2S$. At the other gray levels between, an intermediate value of gas concentration is indicated, In all instances, the gas concentration is a variable which is best measured using the lead acetate strip paper of the present disclosure.

Measurement of $H_2S$ concentration in the immediate vicinity is normally required in petrochemical manufacturing plants and especially at drilling rigs where wells are being drilled into formations suspected of having sour gas. Natural gas is often produced in formations having no fragrance or odor. It is known as sweet gas in that situation. Sour gas however is natural gas which is recovered in the presence of $H_2S$. The response to $H_2S$ depends on the nature of the exposure. For instance, long term, low level exposure may be quite damaging or detrimental. High concentrations of $H_2S$ can be fatal to humans, while smaller or intermediate concentrations can damage plant life, livestock and so on. The human nose responds to the strong pungent fragrance of $H_2S$ in mild concentrations. This equipment however is needed to extend beyond the range of sensitivity of the human nose. For instance, very small or light or trace quantities have a cumulative effect also. The lead acetate tape mechanisms are installed at a number of places around a plant where $H_2S$ is suspected of being present. It is also present in chemical test laboratory equipment and is used in copious quantities in college laboratories in qualitative test procedures. Nevertheless, it is important to measure the exposure of students and workers to the $H_2S$ atmosphere.

Low levels are difficult to measure because they involve very little interaction with lead acetate. It is possible to concentrate the gas that is in the area by collecting more gas in a sample and increasing the flow rate of the gas so that a larger volume of gas sweeps past the lead acetate tape. As more gas is "seen" by the tape, the output data is more significant. Scale factors are thus changed to accommodate some of the limitations in the optical density variations permitted by the lead acetate tape.

The present disclosure is a system which enhances the range of scale values permitted in lead acetate tape. As noted, the tape can be speeded up or slowed down. Also as noted, the amount of air exposed to the tape or the amount of air seen in a time interval by the tape can be raised or lowered by changing the flow rate. The present disclosure however provides a marked extension of the range of the tape so that scale values can be changed significantly. Especially the tape can be made more sensitive at the low end and yet the upper end can be extended so that it does not overload i.e. become difficult to read because the black end point is saturated or overdriven. This disclosure contemplates the addition of a protective layer on top of the tape. The layer serves as an attenuation barrier so that tape exposure is reduced. The hydrogen sulfide molecules are slowed in their diffusion into the tape, thereby retarding the rate or amount or both of the chemical conversion of the lead acetate tape. In other words, the color conversion is modulated in a way to extend the range of the tape dynamically.

The present disclosure is summarized as an improved lead acetate tape. The tape comprises a paper tape formed of felted fibers of cellulose matted into a tape of specified thickness and width. A suitable solvent is used to impregnate the tape with lead acetate. The reactive agent in the solvent is left in the fibers after the solvent has evaporated. The improvement of the present disclosure contemplates the attachment of a backing to the tape of an impervious sheet membrane which prevents exposure from one place, and placement of a porous layer on the opposite or top face. The porous layer serves as a diffusion barrier of specified thickness. This either reduces or retards the time of exposure. It can readily do both, thereby enabling the response of the tape to be stretched over a greater range. This expands the optical density scale involved in reading the tape and makes the tape more responsive over a wide range of values.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a schematic circuit diagram of a tape operated trace gas quantity measuring system and further illustrates a tape transport cooperative with an optical system so that an output is formed having a time based curve exemplified in FIG. 1;

FIG. 2 is a side view of the improved tape of the present disclosure; and

FIG. 3 is a view of a portion of tape showing the face thereof where exposure to the optical measuring system is modified by the incorporation a protective intermediate layer.

DETAILED DESCRIPTION OF THE PREFERRED EMBODIMENT

Attention is now directed to FIG. 1 of the drawings where the numeral 10 identifies a tape measuring system which is responsive to hydrogen sulfide. For this example the gas of interest is hydrogen sulfide and it is measured by lead acetate. The lead acetate is soaked into the tape as will be detailed. The tape of interest for measuring the gas of interest uses the lead acetate, thereby forming a coloration change. This color change is measured and noted through an optical densitometer. It measures the face of the tape for color ranging from the beginning color and point of white to the color end point of black. The range or excursion from white to black is converted into an optical density scale, and that scale is correlated to concentrations of the gas of interest. In this instance, the tape becomes black to a specified level on maximum concentration of $H_2S$. As will be understood, other gases can be detected, and other reactive agents beside the lead acetate can be utilized.

In FIG. 1, the numeral 10 identifies the equipment which is enclosed in a housing 12 which serves a tape transport mechanism. The tape transport mechanism encloses a supply spool 14. This can provide a week's worth of tape, or perhaps a month's supply of tape. The supply spool typically is several hundred feet of tape which is one quarter or perhaps one half inch in width. The supply spool feeds tape to the powered take up spool 16. It is connected to and driven by a motor 18. The motor is operated to provide a specified rate of movement of the tape such as ten inches per second, one inch per second, or 0.1 inches per second. The exposed tape 15 passes through a gap or region 20 where it is exposed to atmosphere. The exposure of the tape 20 in the gap to the atmosphere enables the tape to be contacted by the gas of interest, thereby enabling the equipment to respond and convert the tape 15. This change has the form of a change in color. The color is changed from the white (zero on the optical density scale) and is made blacker by an amount dependent on gas concentration. Optionally, the equipment is installed in a plant where there may be a gas collector apparatus. Typically, that is connected with a gas pump 24. The gas collector 22 delivers the gas through the pump 24 and input through the line 26. It is input to the immediate vicinity of the tape 15 in the exposed window 20. The tape in this region is exposed for interaction with the gas of interest. As noted, exposure of the gas reacts with the tape to change color and thereby form an optical signal of value. The tape is illuminated by a bulb 28 which provides light on the tape and which is reflected from the tape along an optical pathway to an optical measuring device 30. That is connected with a suitable optical density circuit 32. It forms an output to an amplifier 34 and that in turn provides an output signal to a strip chart recorder 36. A representative signal is shown at 40. The signal 40 is a measure of optical density as a function of time. In effect, the measure of optical density is a measure of concentration. As will be understood, there are values of optical density which cannot provide a linear output. When the tape is saturated, it is not possible to make more accurate readings, thereby obtaining a limit to sensitivity.

It is desirable to stretch the optical density range of the present equipment. This can be done by changing any of the several scale factors. One scale factor is tape velocity. Representative values are given at ten inches per second, one inch per second, and 0.1 inch per second. Loosely, changes in the velocity change the exposure time interval. As the tape moves slower, less or smaller concentrations of the gas of interest can be reacted to provide a coloration. This is accomplished to extend the sensitivity downwardly, but maximum saturation is achieved at lower concentrations and so there is some requisite loss of sensitivity.

Scale Factors Controlling Response

One of the scale factors in controlling response is the tape speed. Effectively, this is the time interval during which the tape is exposed in the window 20. In addition, another scale factor is the multiplication of the gas concentration by the gas collector 22, the pump 24 and the supply line 26. By contrast, if the tape is exposed to ambient air with no particular effort to concentrate the gas, a certain sensitivity will be achieved during which the gas of interest is diffused by natural procedures in the vicinity. In this instance, the diffusion of the gas in the vicinity can serve as the baseline, and the gas collector system can enhance the rate of delivery by tenfold, one hundred fold, etc. While all of the above can be done, it still crowds a wide range of excursion into a limited optical density range. The range of optical density (from white which is the zero point to the maximum black which is the ending point) determines the applicable gas concentration range.

The present disclosure sends forth equipment which enhances response of the tape. FIG. 2 shows the tape of the present disclosure. In the ordinary fashion, this tape is comprised of a ribbon 40 of specified width and thickness. It is formed of paper made of felted or matted fibers. They are formed to specify thickness and width. At the time of manufacture, the tape is dipped into a solvent which soaks the tape, making it wet, permitting the solvent to dry. The solvent applies a coating of responsive material, in the instance of this disclosure, it coats lead acetate on the fibers. This combination yields a tape which is responsive over a specified optical density range. The tape can be exposed to hydrogen sulfide from the back face as well as the front face. Even where the tape is thick, i.e., perhaps one or two mils in thickness, the tape color change tends to chemically bleed from back to front or front to back. Thus, hydrogen sulfide exposed to the back face only will nevertheless create a color change seen on the front face. The hydrogen sulfide tends to penetrate readily through the felt fibers making up the paper tape 40. To limit this, the tape 40 is provided with a layer of opaque material 42 on the back face. This can have the form of a sheet of metal foil to pick an example. It is adhesively joined to the paper tape. It need not be very thick because it is there primarily to exclude the $H_2S$ molecules from penetrating from the back face. The foil can be used in lieu of other solid sheet members. A number of such sheet members are available including cellophane, non-porous plastic film and the like. Preferably, they are affixed to the paper tape by a suitable adhesive which is applied between the two sheets. The backing 42 has the same width and length as the tape. This will prevent entry of the molecules into the tape from the backside. On the front side or on the front face more specifically, there is a layer of porous material. The porous layer 44 can have the form of a porous sheet made to a specified thickness. In one example, a sheet of silicone rubber is painted on and permitted to dry. When applied to a specified thickness, it will provide a serpentine air pathway enabling gas molecules to penetrate though the thick layer 44 and eventually come in contact with the paper tape 40. The paper tape 40 is then changed in color depending on the number of molecules which penetrate through the layer 44. This molecular migration will create a lighter shade of color, i.e., it will provide less optical density excursion from the baseline value of white. The lead acetate tape is therefore able to provide an output, but it is time delayed and the intensity is decreased.

The layer 44 can have any one of several different forms including a two part silicone rubber coating which is brushed, dipped, sprayed or adhesively joined in sheet form to the paper tape. It is also possible to use a thin film of polyurethane or latex or other permeable layers. So to speak the permeable layer serves as a dilution barrier. Also, the layer 44 can be thermoplastic and other polymers exemplified by PVC, polyethylene and so on. As will be understood, the mechanics of conversion of the paper tape are relatively straight forward. The tape 40 is first manufactured and impregnated. An adhesive layer is used to join the impervious backing 42. The pervious top layer 44 is applied with an adhesive. Alternately, it can be applied as a wet layer and permitted to dry on the paper tape. The layer 44 can be varied in thickness. For instance, if it is twice as thick, it will provide a greater time delay in exposure of the paper tape 40. It may also reduce the amount of actual gas of interest impinging on the tape. Such a reduction can be obtained by changing the permeability of the layer 44. With larger pores, a greater rate of velocity of penetration can be obtained. Commonly, the layer 44 is clear, or semi-clear so color changes can be seen in the lead acetate.

FIG. 3 of the drawings show another aspect of this. FIG. 3 includes a "sight" area 48. It is the optical spot illuminated by the bulb 28 and viewed by the optical system 30. So to speak, the optics in the measuring system will see only the spot 48. Again, this is a scale factor which is determined by the nature of the optical system. It "sees" the spot of specified width which preferably is smaller than the width of the tape so that the spot fits on the tape. Because this is what is seen, only changes in color in that area are measured. The tape operates in conjunction with the optical system to integrate all the data in the spot 48. As shown in FIG. 3 of the drawings, the sheet of permeable material 44 need not cover the full width of the tape. It is shown with an edge 50 in FIG. 3. The edge can be parallel or cut at an angle to change concentration in response. Examples will make this more clear.

Assume that the layer 44 is applied to a thickness of one mil. If increased to a thickness of two mils, this will stretch out the time required to detect the gas. By doubling the thickness a time delay is implemented. By changing the density of the material 44, attenuation is varied. All the foregoing assumes that the layer 44 is full width; in fact, it can be cut to fifty percent or seventy-five percent or some other specified width. FIG. 3 shows the edge 50 passing through the illuminated optical spot 48 where measurements are made. The amount of light reflected by that spot or region is variable dependent on the amount of the lead acetate which is blackened on exposure to $H_2S$. The optical system will not see the tape 44 or edge 50 in a technical sense; what it will see and integrate is the aggregate light or black fibers in the region 48. In effect, by coating the layer 44 on part half of the tape, the response range (meaning optical density range from the least to the largest) is stretched out or made wider in terms of optical density correlated to gas concentration. In other words, this kind of system stretches the optical density range by making the end points farther apart in a given situation.

In general terms, it is therefore desirable to describe the layer 44 as a layer applied to the paper strip 40 with variations in thickness to extend the time of penetration, with variations in porosity to reduce the amount actually penetrating, and variations in width to encourage range stretching in the manner just described. The tape system set forth by the present disclosure thus uses the layer 44 to expand the effective sensitivity range.

While the forgoing is directed to the preferred embodiment of the present invention, other and further embodiments of the invention may be devised without departing from the basic scope thereof, and the scope thereof is determined by the claims which follow.

What is claimed is:

1. A treated tape responsive to a gas of interest which changes colors to indicate the concentration of the gas of interest comprising:

an elongate tape having a responsive element therein changing colors in the presence of the gas of interest wherein the responsive element is lead acetate and the gas of interest is hydrogen sulfide;

a permeable layer on the tape which retards exposure to the gas of interest; and an imprevious backing joined on the back face of the tape.

2. The apparatus of claim 1 wherein said layer is transparent.

3. The apparatus of claim 1 wherein said layer is adhesively joined at the tape.

4. The apparatus of claim 1 wherein said layer has a width less than said tape.

5. The apparatus of claim 1 wherein said layer is applied to a specified thickness to retard the has of interest.

6. A treated tape responsive to a gas of interest which changes colors to indicate the concentration of the gas of interest comprising:

an elongate tape having a responsive element therein changing colors in the presence of the gas of interest wherein the responsive element is lead acetate and the gas of interest is hydrogen sulfide;

a tape covering layer of specified thichkness; and an impervious backing joined on the back face of the tape.

7. The apparatus of claim 6 wherein said layer has a width less than said tape.

8. The apparatus of claim 6 wherein said layer is applied to a specified thickness to retard the has of interest.

9. The apparatus of claim 6 wherein said layer is transparent.

10. The apparatus of claim 9 wherein said layer is adhesively joined at the tape.

11. A treated tape responsive to a gas of interest which changes colors to indicate the concentration of the gas of interest comprising:

an elongate tape having a responsive element therein changing colors in the presence of the gas of interest wherein the responsive element is lead acetate and the gas of interest is hydrogen sulfide;

a layer having a width less than the width of the tape; and an impervious backing joined on the back face of the tape.

12. The apparatus of claim 11 wherein said layer is transparent.

13. The apparatus of claim 12 wherein said layer is adhesively joined at the tape.

14. The apparatus of claim 13 wherein said layer is applied to a specified thickness to retard the has of interest.

* * * * *